United States Patent
Stevenson et al.

(10) Patent No.: US 6,566,978 B2
(45) Date of Patent: May 20, 2003

(54) FEEDTHROUGH CAPACITOR FILTER ASSEMBLIES WITH LEAK DETECTION VENTS

(75) Inventors: Robert A. Stevenson, Canyon Country, CA (US); Matthew A. Dobbs, Gardnerville, NV (US)

(73) Assignee: Greatbatch-Sierra, Inc., Clarence, NY (US)

( * ) Notice: Subject to any disclaimer, the term of this patent is extended or adjusted under 35 U.S.C. 154(b) by 0 days.

(21) Appl. No.: 09/733,342

(22) Filed: Dec. 7, 2000

(65) Prior Publication Data

US 2002/0027484 A1 Mar. 7, 2002

Related U.S. Application Data

(63) Continuation-in-part of application No. 09/657,123, filed on Sep. 7, 2000, now Pat. No. 6,529,103.

(51) Int. Cl.⁷ .................................................. H03H 7/01
(52) U.S. Cl. .................... 333/182; 333/185; 361/302
(58) Field of Search ................................ 333/182, 183; 361/302; 607/36, 37

(56) References Cited

U.S. PATENT DOCUMENTS

| | | | |
|---|---|---|---|
| 2,756,375 A | 7/1956 | Peck | 361/302 |
| 3,235,939 A | 2/1966 | Rodriguez et al. | |
| 3,538,464 A | 11/1970 | Walsh | 333/182 |
| 3,920,888 A | 11/1975 | Barr | |
| 4,083,022 A | 4/1978 | Nijman | 333/182 |
| 4,144,509 A | 3/1979 | Boutros | 333/181 |
| 4,148,003 A | 4/1979 | Colburn et al. | 333/181 |
| 4,152,540 A | 5/1979 | Duncan et al. | 361/302 X |
| 4,220,813 A | 9/1980 | Kyle | |
| 4,247,881 A | 1/1981 | Coleman | 361/302 |
| 4,314,213 A | 2/1982 | Wakino | 333/182 |
| 4,352,951 A | 10/1982 | Kyle | |
| 4,362,792 A | 12/1982 | Bowsky et al. | |
| 4,424,551 A | 1/1984 | Stevenson et al. | 361/302 |
| 4,853,824 A * | 8/1989 | Tsuzurahara | 333/182 X |
| 5,333,095 A | 7/1994 | Stevenson et al. | 361/302 |
| 5,751,539 A | 5/1998 | Stevenson et al. | 361/302 |
| 5,825,608 A * | 10/1998 | Duva et al. | 361/302 |
| 5,905,627 A | 5/1999 | Brendel et al. | 361/302 |
| 5,973,906 A | 10/1999 | Stevenson et al. | 361/302 |
| 6,008,980 A | 12/1999 | Stevenson et al. | 361/302 |
| 6,349,025 B1 * | 2/2002 | Fraley et al. | 361/302 |

* cited by examiner

Primary Examiner—Justin P. Bettendorf

(57) ABSTRACT

A feedthrough capacitor filter assembly includes a capacitor having first and second sets of conductive electrode plates embedded within an insulative or dielectric body, and a leak detection vent for facilitated hermetic seal testing prior to use. At least one feedthrough terminal pin extends through the capacitor in conductive relative with the first set of electrode plates, and an outer ferrule is mounted about the capacitor in conductive relation with the second set of electrode plates. A hermetic seal is seated within the ferrule at one side of the capacitor to prevent leakage of fluid through the filter assembly. The hermetic seal is spaced from a face of the capacitor to form a gap therebetween.

57 Claims, 10 Drawing Sheets

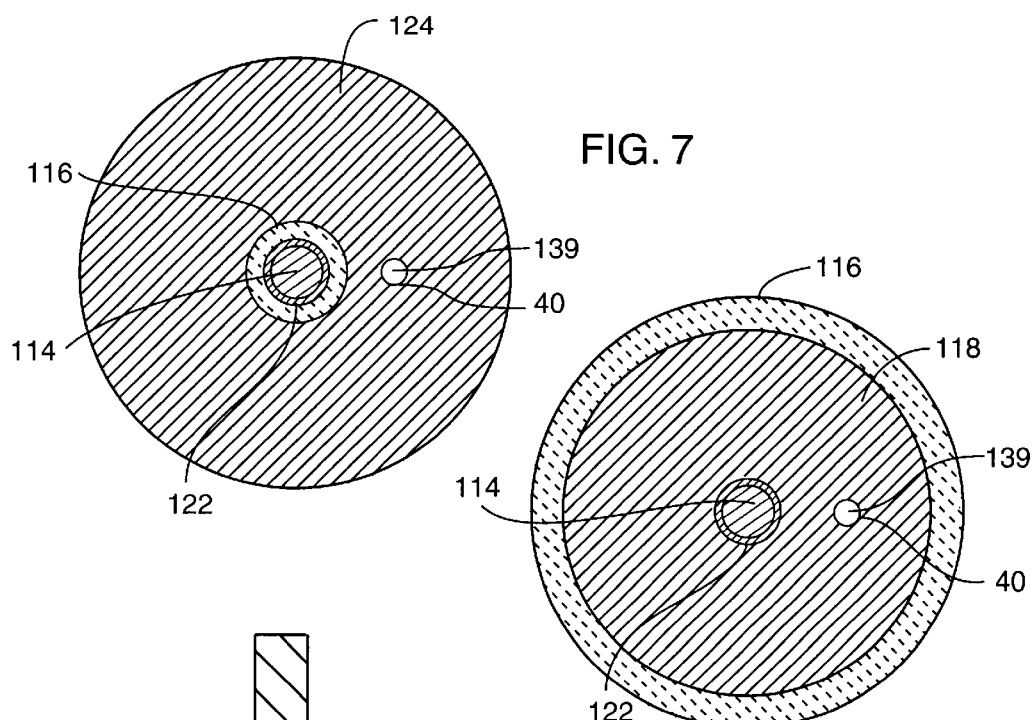
FIG. 7
FIG. 8
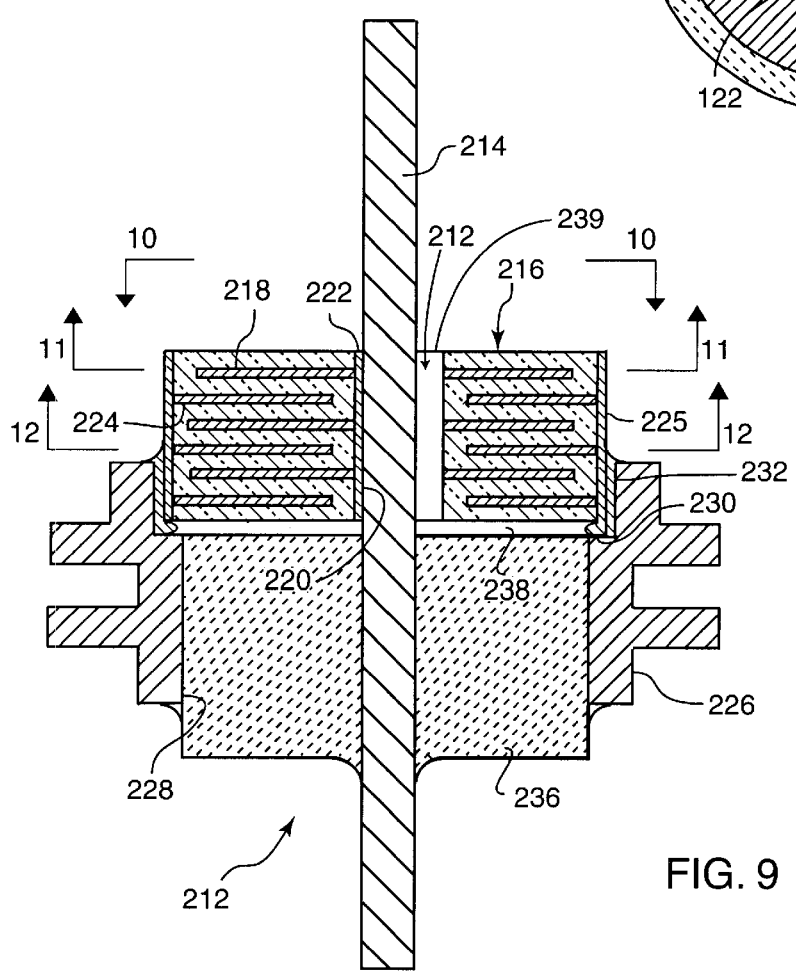
FIG. 9

FEEDTHROUGH CAPACITOR FILTER ASSEMBLIES WITH LEAK DETECTION VENTS

RELATED APPLICATION

This is a continuation-in-part of U.S. patent application Ser. No. 09/657,123, filed Sep. 7, 2000, now U.S. Pat. No. 6,529,103, entitled INTERNALLY GROUNDED FEEDTHROUGH FILTER CAPACITOR WITH IMPROVED GROUND PLANE DESIGN FOR HUMAN IMPLANT AND OTHER APPLICATIONS.

BACKGROUND OF THE INVENTION

This invention relates generally to feedthrough capacitor filter assemblies, particularly of the type used in implantable medical devices such as cardiac pacemakers, cardioverter defibrillators and the like, to decouple and shield internal electronic components of the medical device from undesirable electromagnetic interference (EMI) signals. More specifically, this invention relates to an improved feedthrough capacitor filter assembly of the type incorporating a hermetic seal to prevent passage or leakage of fluids through the filter assembly, wherein a leak detection passage is provided to accommodate and facilitate post-manufacture and pre-usage testing of the hermetic seal.

Feedthrough terminal pin assemblies are generally well known in the art for use in connecting electrical signals through the housing or case of an electronic instrument. For example, in implantable medical devices such as cardiac pacemakers, defibrillators and the like, the terminal pin assembly comprises one or more conductive terminal pins supported by an insulator structure for feedthrough passage of electrical signals from the exterior to the interior of the medical device. Many different insulator structures and related mounting methods are known for use in medical devices wherein the insulator structure provides a hermetic seal to prevent entry of patient body fluids into the medical device housing, where such body fluids could otherwise interfere with the operation of and/or cause damage to internal electronic components of the medical device.

In the past, two primary technologies have been employed to manufacture the hermetic seal. One technique involves the use of an alumina insulator which is sputtered to accept brazing material. This alumina insulator is brazed to the terminal pin or pins, and also to an outer metal ferrule of titanium or the like. The alumina insulator supports the terminal pin or pins in insulated spaced relation from the ferrule which is adapted for suitable mounting within an access opening formed in the housing of the medical device. In an alternative technique, the hermetic seal comprises a glass-based seal forming a compression or fused glass seal for supporting the terminal pin or pins within an outer metal ferrule.

The feedthrough terminal pins are typically connected to one or more lead wires which, in the example of a cardiac pacemaker, sense signals from the patient's heart and also couple electronic pacing pulses from the medical device to the patient's heart. Unfortunately, these lead wires can act as an antenna to collect stray electromagnetic interference (EMI) signals for transmission via the terminal pins into the interior of the medical device. Such unwanted EMI signals can disrupt proper operation of the medical device, resulting in malfunction or failure. For example, it has been documented that stray EMI signals emanating from cellular telephones can inhibit pacemaker operation, resulting in asynchronous pacing, tracking and missed beats. To address this problem, hermetically sealed feedthrough terminal pin assemblies have been designed to include a filter capacitor for decoupling EMI signals in a manner preventing such unwanted signals from entering the housing of the implantable medical device. See, for example, U.S. Pat. Nos. 4,424,551; 5,333,095; 5,751,539; 5,905,627; 5,973,906; and 6,008,980.

While feedthrough capacitor filter assemblies have provided a significant advance in the art, one potential area of concern is that the filter capacitor is often incorporated into the terminal pin assembly in a way that can mask a defective hermetic seal. More particularly, a defective braze or a defective glass-based seal structure, which would permit undesirable leakage of patient body fluids when mounted on a medical device and implanted into a patient, can be obstructed by the mounting of the filter capacitor and its associated electromechanical connections. For example, with reference to the feedthrough filter capacitor shown in U.S. Pat. No. 4,424,551, a ceramic filter capacitor is bonded to a glass seal and then embedded in epoxy material. Typical post-manufacture leak testing is performed by mounting the feedthrough assembly in a test fixture, and then subjecting one side of the feedthrough assembly to a selected pressurized gas such as helium. While the bulk permeability of the epoxy material is such that helium under pressure can penetrate therethrough in the presence of a defective hermetic seal, the duration of this pressure test (typically a few seconds) is often insufficient to permit such penetration. Accordingly, the epoxy material can mask the defective hermetic seal. The thus-tested feedthrough assembly can then mistakenly be incorporated into a medical device and implanted into a patient, wherein slow leakage of patient body fluids through the feedthrough assembly can cause the medical device to malfunction or fail.

The present invention is directed to an improved feedthrough capacitor filter assembly suitable for use in an implantable medical device or the like, wherein the feedthrough assembly includes a leak detection passageway for accommodating and facilitating post-manufacture hermetic seal testing.

SUMMARY OF THE INVENTION

In accordance with the invention, an improved feedthrough capacitor filter assembly is provided for use in human implant applications and the like, such as in a cardiac pacemaker or defibrillator, wherein the filter assembly includes a leak detection passage for facilitated hermetic seal testing subsequent to manufacture and prior to use.

In one form, the feedthrough capacitor filter assembly comprises a capacitor having first and second sets of conductive electrode plates embedded within an insulative or dielectric body such as a monolithic ceramic body. At least one feedthrough terminal pin extends through the capacitor in conductive relation with the first set of electrode plates. An outer ferrule is mounted about the capacitor in conductive relation with the second set of electrode plates. A hermetic seal formed typically of an alumina insulator or a fused glass dielectric material is seated within or over the ferrule at one side of the capacitor, in hermetically sealed relation with the ferrule and the at least one terminal pin to prevent leakage of fluid, such as patient body fluid in a human implant application, through the filter assembly. A leak detection vent is formed in the assembly to accommodate and facilitate post-assembly fluid leak testing of the hermetic seal, as by subjecting the hermetic seal to a selected pressurized test gas such as helium or the like, prior to implantation of the filter assembly in a medical device into a patient.

In several of the preferred embodiments, the hermetic seal and the capacitor are separated by a short gap by a dissolvable washer. This gap provides a leak detection vent which facilitates detecting the presence of the test gas leaking past the hermetic seal. In other preferred embodiments of the invention, a leak detection passage is provided through the capacitor which further facilitates detecting the presence of the test gas leaking past the hermetic seal into the gap.

Other features and advantages of the invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 7 is a sectional view taken generally on the line 7—7 of FIG. 6;

FIG. 8 is a sectional view taken generally on the line 8—8 of FIG. 6;

FIG. 9 is a sectional view similar to FIG. 6, but depicting a further alternative preferred embodiment of the invention;

DETAILED DESCRIPTION OF THE PREFERRED EMBODIMENTS

Figure 1:
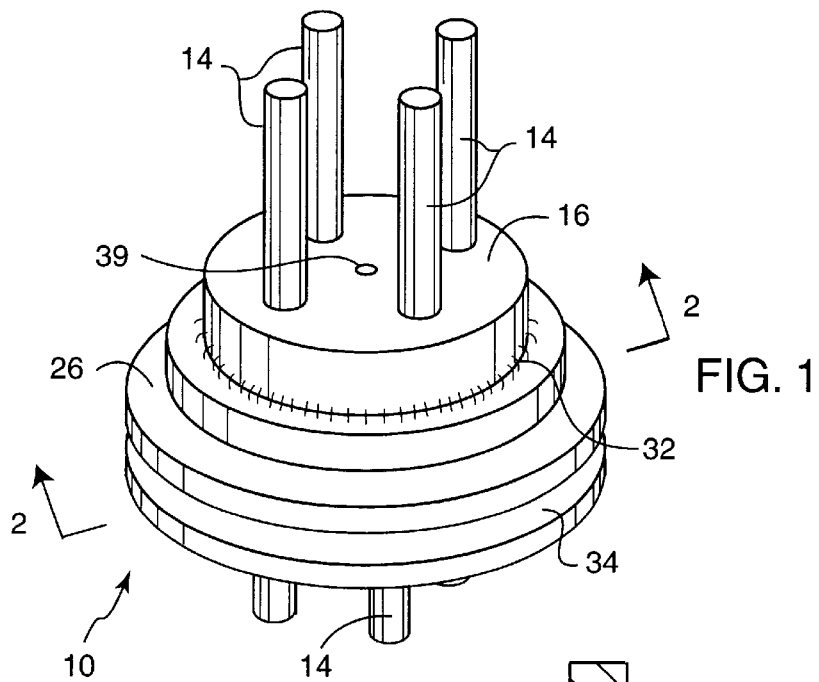
FIG. 1 is a perspective view of a feedthrough capacitor filter assembly embodying the novel features of the invention.

As shown in the exemplary drawings, an improved feedthrough capacitor filter assembly referred to generally by the reference numeral 10 in FIGS. 1–4 is provided for use in an implantable medical device of the like (not shown) for suppressing or decoupling undesired electromagnetic interference (EMI) signals and/or noise transmission into the interior of the medical device. The feedthrough filter assembly 10 is particularly designed for use in a cardiac pacemaker or defibrillator or the like, for coupling, transmitting and/or receiving electrical signals to and from a patient's heart, while hermetically sealing the interior of the medical instrument against ingress of patient body fluids which could otherwise disrupt instrument operation or cause instrument malfunction. In accordance with the invention, the improved feedthrough filter assembly 10 includes a leak detection vent 12 which permits effective and reliable post-manufacture hermetic seal testing of the filter assembly 10 prior to implantation with the associated medical device into the body of a patient. Accordingly, any filter assembly 10 having a defective hermetic seal can be accurately identified and rejected prior to use in a patient.

FIGS. 1–4 illustrate the feedthrough capacitor filter assembly 10 in one preferred form, comprising a so-called quad polar configuration having four separate conductive terminal pins 14 extending through a discoidal-shaped capacitor body 16. More specifically, as shown best in FIGS. 2–4, the capacitor body 16 comprises a unitized dielectric structure such as a ceramic or ceramic-based monolith having multiple capacitor-forming conductive electrode plates formed therein. In the quad polar example as shown, these electrode plates include a plurality of spaced-apart layers of first or "active" electrode plates 18 (FIGS. 2 and 4), wherein each such layer is subdivided into four spaced-apart and generally pie-shaped electrode plates 18. Accordingly, the four electrode plates 18 of each layer group are electrically insulated from each other by the dielectric material of the capacitor body 16. The multiple spaced-apart layers of the first or "active" electrode plates 18 are formed with their respective electrode plates 18 in stacked alignment with the respective electrode plates 18 of overlying and underlying layers to define four respective "active" plate stacks. The four terminal pins 14 respectively pass generally centrally through bores 20 formed in these "active" plate stacks, and are conductively coupled to the associated stacked set of electrode plates 18 by a suitable conductive surface lining such as a surface metallization layer 22 (FIG. 2) or the like lining each bore 20.

Figure 2:
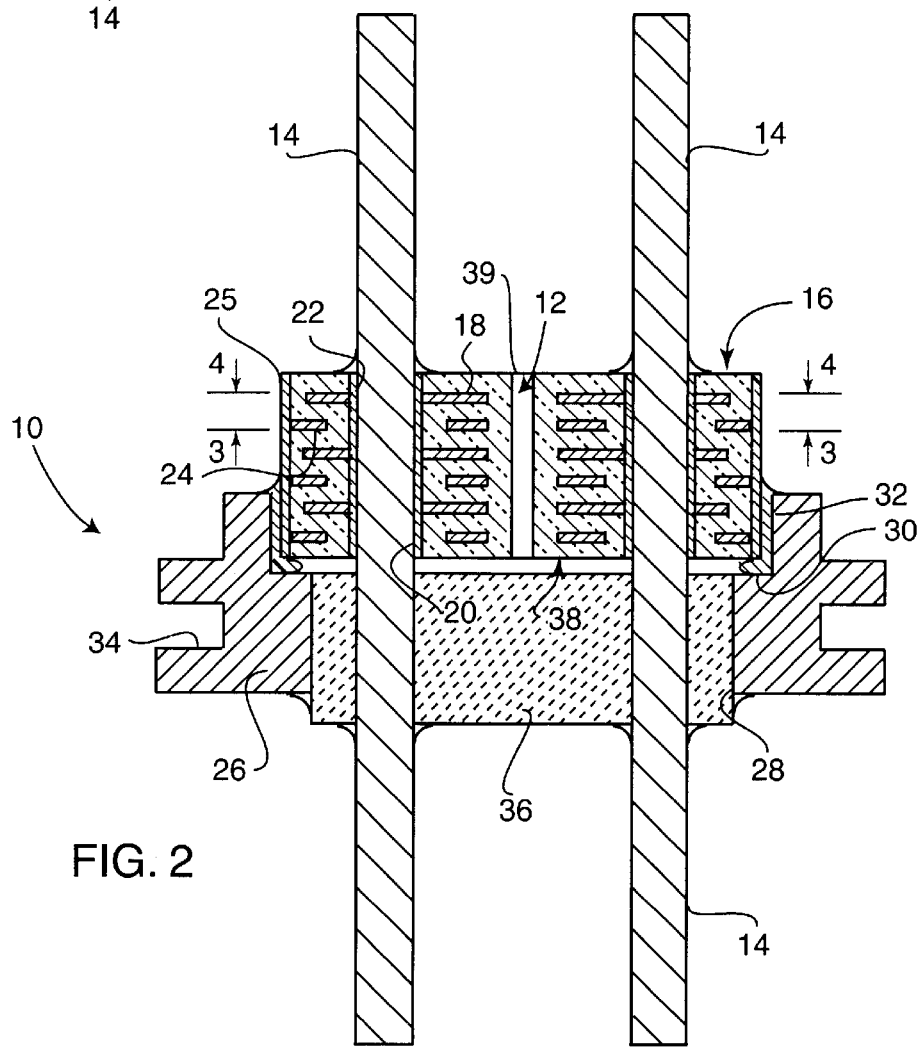
FIG. 2 is an enlarged sectional view taken generally on the line 2—2 of FIG. 1.
Figure 3:
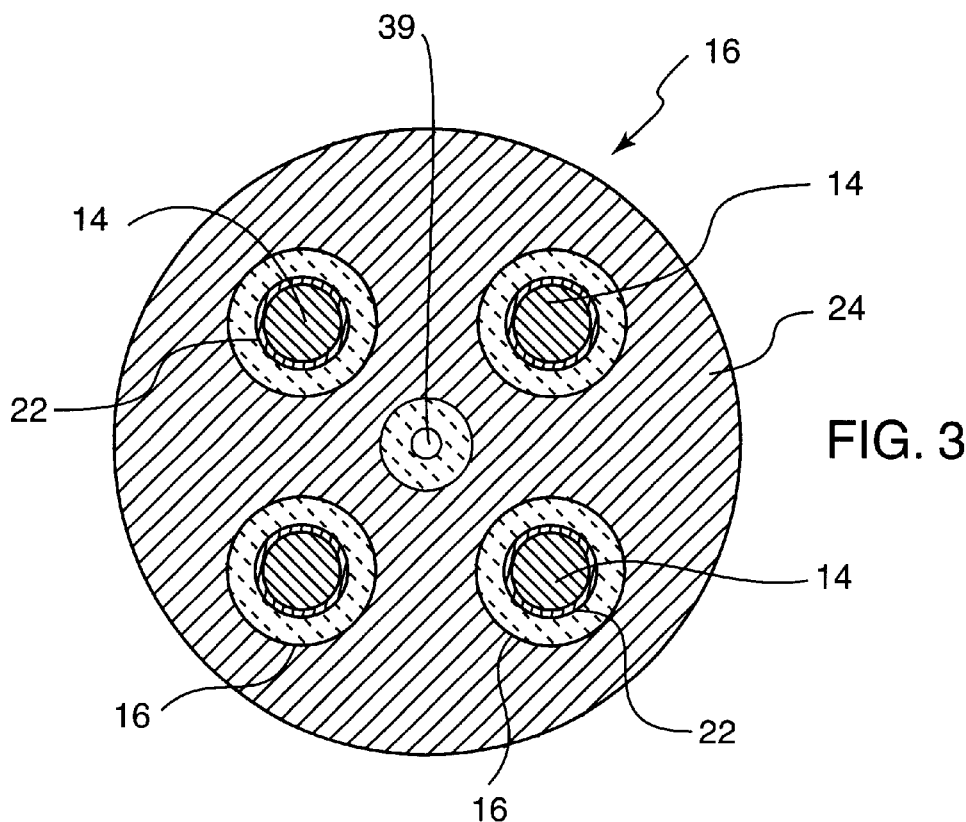
FIG. 3 is a sectional view taken generally on the line 3—3 of FIG. 2.

A plurality of spaced-apart layers of second or "ground" electrode plates 24 are also formed within the capacitor body 16, in stacked relation alternating or interleaved with the layers of "active" electrode plates 18 (FIGS. 2 and 3). These "ground" electrode plates include outer perimeter edges which are exposed at the outer periphery of the discoidal capacitor body 16 where they are electrically connected in parallel by a suitable conductive surface such as a surface metallization layer 25. Importantly, however, the outer edges of the first or "active" electrode plates 18 terminate in spaced relation with the outer periphery of the capacitor body 16, whereby the "active" electrode plates are electrically isolated by the capacitor body from the conductive layer 25 coupled to the "ground" electrode plates 24. Similarly, the "ground" electrode plates 24 have inner edges which terminate in spaced relation with the terminal pin bores 20, whereby the "ground" electrode plates are electrically isolated by the capacitor body from the terminal pins 14 and the conductive layer 22 lining the pin bores 20. The number of "active" and "ground" electrode plates 18 and 24, together with the dielectric thickness or spacing therebetween may vary in accordance with the desired capacitance value and voltage rating.

The thus-assembled capacitor body 16 with terminal pins 14 supported thereby and extending therethrough is assembled with a conductive outer ferrule 26 (FIGS. 1 and 2). In the exemplary drawings, the outer ferrule 26 comprises a generally ring-shaped structure formed from a suitable biocompatible conductive material, such as titanium or a titanium alloy, and is shaped to define a central aperture 28 with a counterbore segment forming a radially inwardly extending step or shoulder 30. The capacitor body 16 has a size and shape for nested and slidable reception into the ferrule aperture 28, with a peripheral rim thereof seated upon the internal shoulder 30 as shown best in FIG. 2. The capacitor body 16 is securely mounted in this position by an annular bead 32 of conductive material, such as a solder or braze ring, or thermal-setting conductive adhesive or the like, for electrically connecting the "ground" plates 24 to the conductive ferrule 26. Accordingly, the capacitor body 16 is positioned to extend generally across and to close the central aperture 28 in the ferrule 26. As shown, the outer ferrule 26 additionally includes a ring-shaped, radially outwardly opening channel 34 for facilitated assembly with a test fixture (not shown) for hermetic seal testing as will be described further herein, and also for facilitated assembly with the housing (also not shown) on an implantable medical device or the like.

A hermetic seal 36 is also positioned within the ferrule aperture 28 to prevent passage of fluid such as patient body fluids through the feedthrough filter assembly 10 during normal use implanted within the body of a patient. More specifically, the hermetic seal 36 comprises an electrically insulating or dielectric structure such as an alumina or fused glass type or ceramic-based insulator installed within the ferrule aperture 28 at one axial side of the capacitor body 16. In the preferred form, the hermetic seal 36 is positioned relative to the adjacent axial side of the capacitor body 16 and cooperates therewith to define a short axial gap 38 therebetween (FIG. 2). This axial gap 38 forms a portion of the leak detection vent 12 and facilitates leak detection which will be described in greater detail below. The hermetic seal 36 thus defines an inboard face presented in a direction axially toward the adjacent capacitor body 16, and an opposite outboard face presented in a direction axially away from the capacitor body. The hermetic seal 36 desirably forms a fluid-tight seal about the inner diameter surface of the conductive ferrule 26, and also forms a fluid-tight seal about each of the four terminal pins 14. The hermetic seal 36 thus prevents fluid migration or leakage through the ferrule 26, along any of the structure interfaces between components mounted within the ferrule, while maintaining the terminal pins 14 electrically insulated with respect to each other and also with respect to the ferrule 26.

Figure 4:
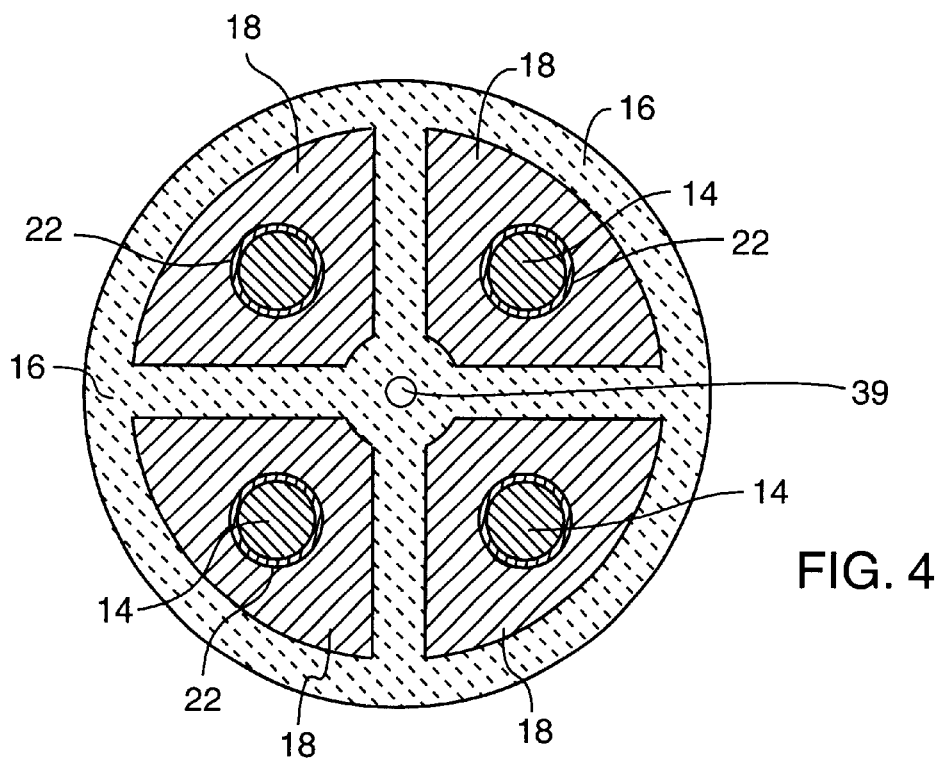
FIG. 4 is a sectional view taken generally on the line 4—4 of FIG.
Figure 5:
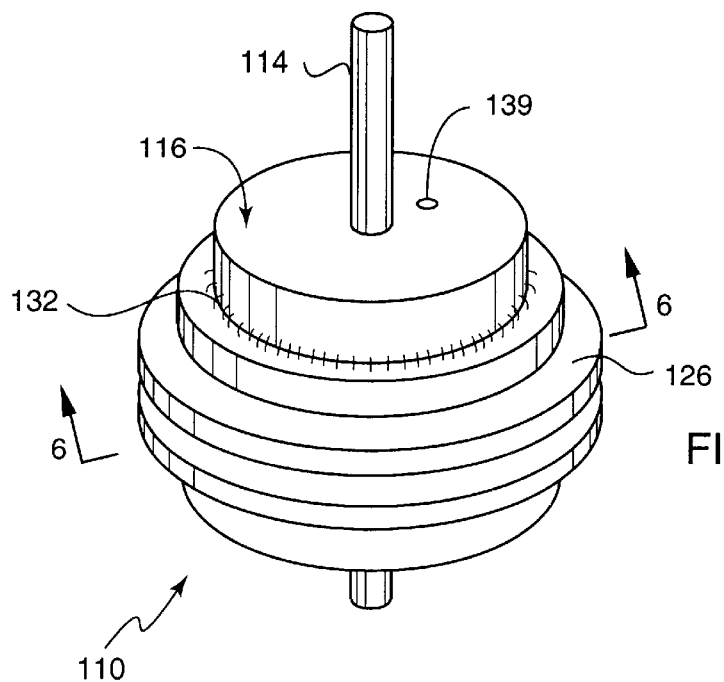
FIG. 5 is a perspective view of a feedthrough filter capacitor assembly constructed in accordance with one alternative preferred form of the invention.

In addition to the gap 38, the leak detection vent 12 includes a passage 39 which extends axially through the capacitor body 16 for venting the gap 38 to the exterior of the capacitor body. FIGS. 1–4 show the leak detection passage 39 extending along a central axis of the discoidal capacitor body 16, wherein this passage 39 may be formed economically and in precision manner using automated drilling fixtures (not shown) of a type known in the art. FIGS. 3 and 4 show the leak detection passage 39 defining an inner diameter surface which is physically spaced from and thus electrically insulated by the capacitor body material from the sets of electrode plates 18 and 24. This inner diameter surface of the leak detection passage 39 is illustrated in spaced relation with the sets of electrode plates 18 and 24, although it will be appreciated that edges of the "ground" electrode plates 24 may be exposed within the passage 39 and/or the passage 39 may include a conductive lining such as a surface metallization lining for more effective decoupling of EMI signals from the interior of an associated electronic instrument.

The resultant feedthrough capacitor filter assembly 10, including the leak detection vent 12, can be subjected quickly and reliably to a leak detection step prior to assembly and use thereof in an implantable medical device or the like. More particularly, the outer ferrule 26 can be clamped into a test fixture (not shown) defining a gas pressure chamber on the hermetic seal side of the filter assembly 10. By elevating the pressure of a selected test gas such as helium or the like within the pressure chamber, the hermetic seal 36 and its associated connections with the terminal pins 14 and the ferrule 26 are subjected to the gas under pressure. Any leakage of the test gas along or between these structures will result in gas migration to the gap 38, wherein such leaking gas can flow readily and freely to and through the leak detection passage 39 for detection by means of a suitable monitor (not shown). In this regard, in one preferred method, the selected test gas comprises helium, and the associated monitor is designed to detect the presence of helium leaking past the hermetic seal 36 to the gap 38, and further through the passage 39. Accordingly, a defective hermetic seal 36 can be rapidly and accurately identified before the filter assembly 10 is assembled with a medical device and implanted into the body of a patient. Thus, potentially catastrophic consequences associated with a leaking hermetic seal in an implanted device can be avoided.

Another benefit of providing a leak detection vent 12 comprising the axial gap 38 and the passage 39 is realized when cleaning the assembled feedthrough capacitor filter assembly 10 following assembly of the component parts. In this regard, it is sometimes desirable to be able to inject methylene chloride under the capacitor for cleaning. The passage 39 provides suitable access for injecting methylene chloride into the gap 38 between opposed faces of the capacitor and the hermetic seal.

The passage 39 can also be used for solvent flushing, cleaning a soldering flux that would be trapped between the capacitor and its mounting surface, baking out any entrapped solvents allowing them to de-gas, backfilling with a thermosetting material such as an epoxy or backfilling with a silicone or other material to eliminate any air space between the capacitor and its mounting surface. The passage 39 also allows for vacuum removal of air, moisture and other gases that may be trapped between the capacitor and its mounting surface. In a typical implantable medical device such as a pacemaker and implantable cardioverter defibrillator after installation of the filtered hermetic terminal by lazer welding, it is common in the industry fort he entire titanium housing and package to be vacuum evacuated and then backfilled with an inert gas such as nitrogen or combinations of nitrogen and argon. This is an important protection for the internal electronic components in that they are able to operate for many years in a completely moisture free environment. Accordingly, the passage 39 allows for the vacuum to also reach the space between the capacitor and its mounting surface and also to be backfilled.

An alternative preferred form on the invention is shown in FIGS. 5–8, wherein components corresponding structurally and functionally to those shown and described in FIGS. 1–4 are identified by common reference numerals increased by 100. FIGS. 5–8 illustrate a modified feedthrough capacitor filter assembly 110 including a single feedthrough terminal pin 114.

More specifically, the modified filter assembly 110 includes a discoidal-shaped capacitor body 116 formed to encase first or "active" electrode plates 118 in a stacked and alternating array with a corresponding number of second or "ground" electrode plates 124. The "active" electrode plates 118 include inner edges exposed along the length of an axially extending bore 120 including a surface metallization layer 122 for conductively coupling the plates 118 in parallel to the conductive terminal pin 114. The "ground" electrode plates 124 include outer edges exposed along the length of an outer periphery of the capacitor body 116 which includes a surface metallization layer 125 for conductively coupling the plates 124 in parallel to an outer ferrule 126. In this regard, the outer ferrule 126 comprises a ring-shaped structure defining a central aperture 128 therethrough, with an internal shoulder 130 for seated and conductive connection with the "ground" electrode plates 124 by means of a conductive annular bead 132 or the like. A hermetic seal 136 is also positioned within the ferrule 126 at one axial side of the capacitor body 116, preferably to form a short axial gap 138 therebetween.

Figure 6:
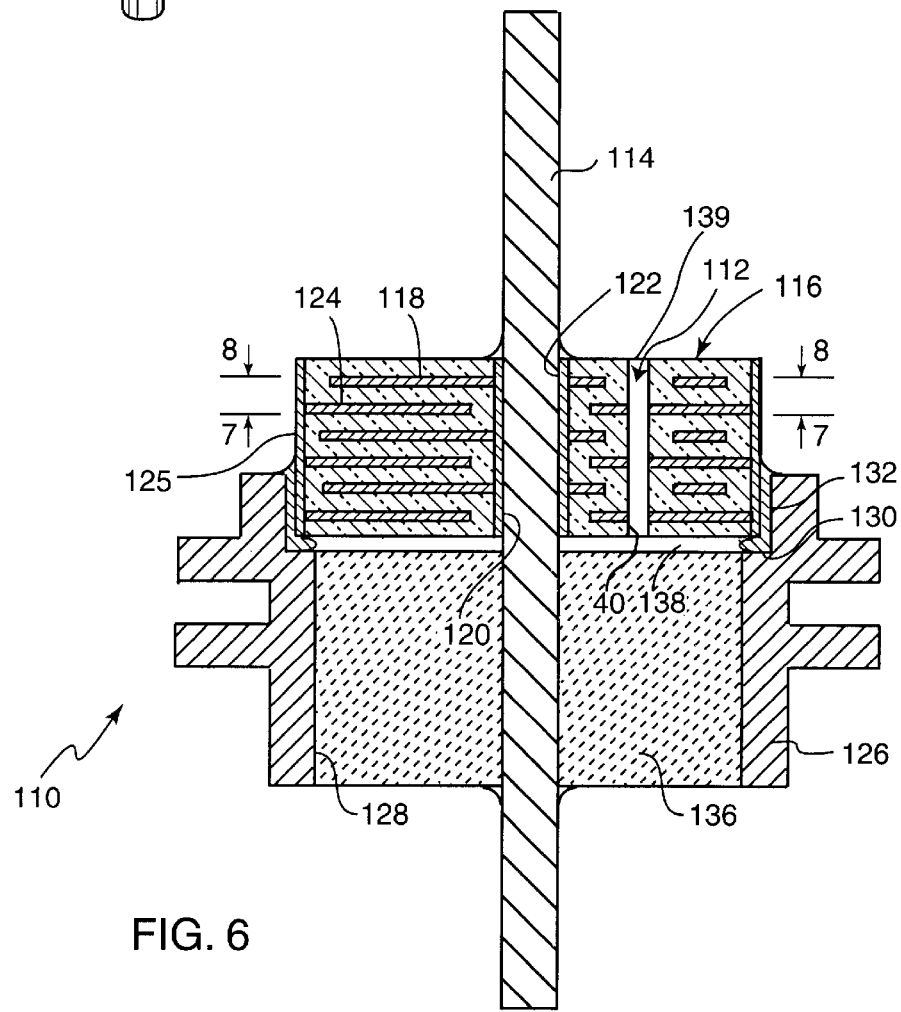
FIG. 6 is an enlarged sectional view taken generally on the line 6—6 of FIG. 5.
Figure 10:
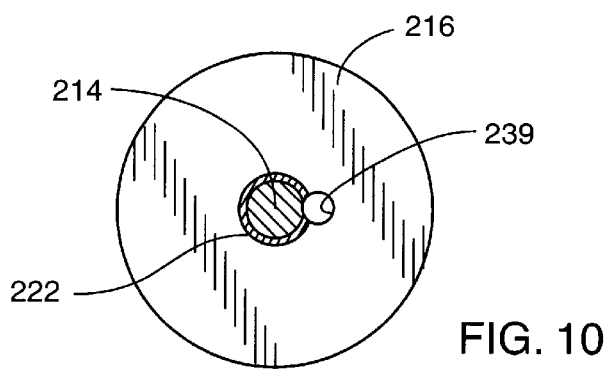
FIG. 10 is a sectional view taken generally on the line 10—10 of FIG. 9.
Figure 11:
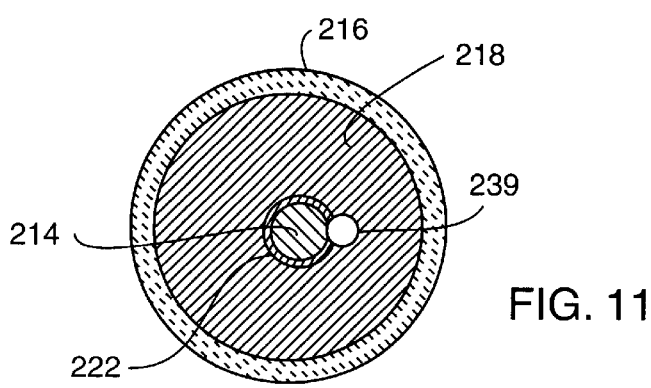
FIG. 11 is a sectional view taken generally on the line 11—11 of FIG. 9.
Figure 12:
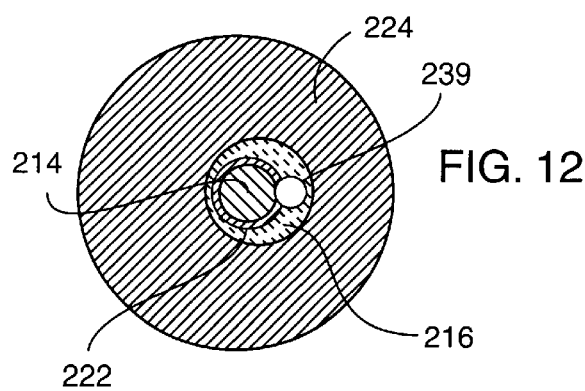
FIG. 12 is a sectional view taken generally on the line 12—12 of FIG. 9.
Figure 13:
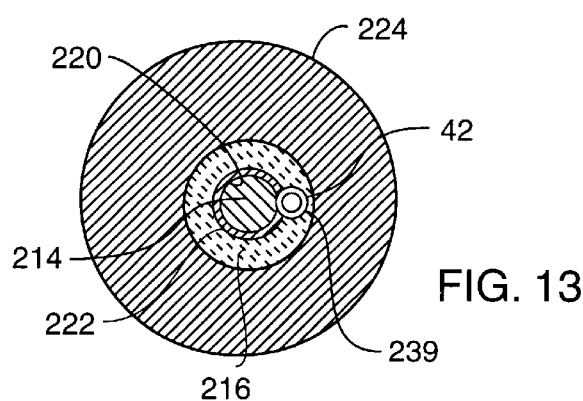
FIG. 13 is a sectional view similar to FIG. 12, but illustrating a further alternative preferred form of the invention.

FIGS. 6–8 show a leak detection passage 139 formed through the capacitor body 116 in a position offset from an axial centerline of the capacitor body. In this version of the invention, edges of the "ground" electrode plates 124 are exposed at the leak detection passage 139, and a conductive lining 40 of surface metallization or the like is provided to couple the "ground" electrode plates 124 together within the passage 139. Alternately, the "active" electrode plates 118 may have edges exposed within the leak detection passage 139. In either geometry, from an electromagnetic standpoint, this has the effect of providing a wave-guide cut-off to block undesired EMI signals at higher frequencies, in comparison with the embodiment of FIGS. 1–4. The feedthrough capacitor filter assembly 110 can be tested quickly and reliably, in the same manner described above with respect to FIGS. 1–4 to identify a defective hermetic seal 136 prior to installation of the filter assembly into an implantable medical device or the like.

Another alternative preferred form of the invention is depicted in FIGS. 9–12, wherein components corresponding structurally and functionally to those shown and described in FIGS. 1–4 are identified by common reference numerals increased by 200. As shown, a modified feedthrough capacitor filter assembly 210 again includes a single feedthrough terminal pin 214.

In this embodiment (FIGS. 9–12), the terminal pin 214 extends through an axially centered pin bore 220 formed in a capacitor body 216, wherein a portion of the pin bore 220 is lined by a surface metallization layer 222 for electrically coupling the pin 214 with a spaced-apart plurality of first or "active" electrode plates 218. These electrodes plates 218 are arranged in an alternating stack with a corresponding plurality of second or "ground" electrode plates 224 having outer edges exposed at the periphery of the capacitor body 216 for electrical connection to a surface metallization layer 225. The capacitor body 216 is mounted within a shallow counterbore formed in a ring-shaped outer ferrule 226, by means of a conductive bead 232 or the like. A hermetic seal 236 is also formed within a central aperture 228 of the ferrule 226 and cooperates with the capacitor body 216 to define a short axial gap 238 therebetween.

FIGS. 9–12 show the leak detection passage 239 formed through the capacitor body 216 as an axial offset enlargement disposed at one side of the pin bore 220. The resultant feedthrough filter assembly 210, as viewed in FIG. 9, can be subjected to pre-installation hermetic seal testing in the same manner as previously described.

Figure 14A:
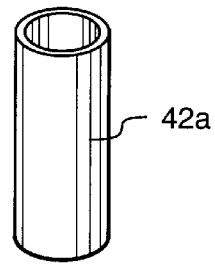
FIGS. 14A, 14B and 14C are respective perspective views of a plurality of leak detection passage-forming inserts for mounting into the embodiment depicted in FIG. 13.
Figure 14B:
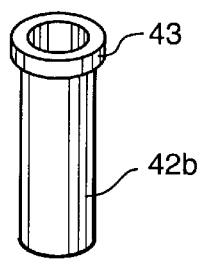
Figure 14C:
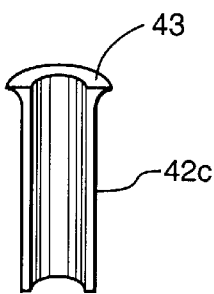

FIGS. 13 and 14A–14C illustrate a variation of the embodiment of FIGS. 9–12, wherein a sleeve-type insert 42 (FIG. 13) can be fitted through the leak detection passage 239 to isolate the leak detection passage from the central pin bore 220. This insert 42 can be formed from an electrically insulating or electrically conducting material, as desired. FIG. 14A shows one preferred form of the insert, comprising a straight cylindrical sleeve 42a. FIG. 14B shows another preferred insert geometry in the form of a straight cylindrical sleeve 42b having a short radially outwardly projecting flange 43 at one axial end thereof. FIG. 14C shows still another preferred insert configuration as a half-cylinder 42c having a short radially outwardly projecting flange 43 at one axial end thereof. The half-cylinder insert 43c of FIG. 14C would be installed into the leak detection passage 239 in an orientation with the open side facing radially outwardly from the pin bore 220. Such inserts 42a–c may be used in instances wherein the capacitor body 216 is conformally coated or embedded in a polymer overcoat or the like. The sleeve-like insert 42a–c could provide a passageway for leak detection gases through the capacitor body and also through the polymer overcoating. In some cases, the insert 42a–c could be removed following curing of the polymer overcoating, in which case the insert 42a–c would desirably be formed from a non-adherent material such as Teflon.

Figure 15:
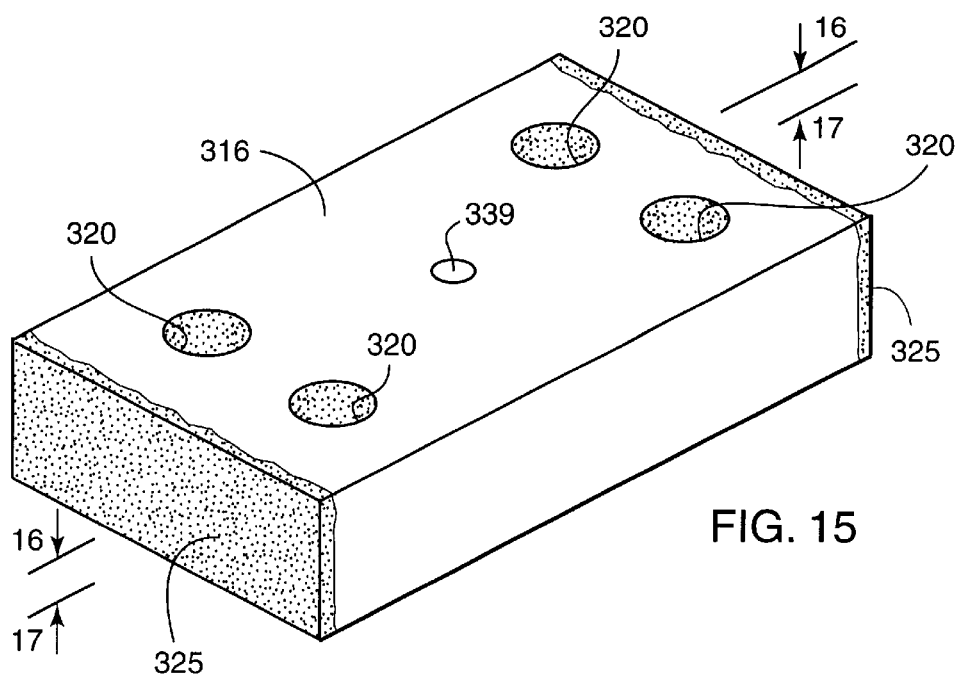
FIG. 15 is a perspective view of a capacitor showing features of another modified preferred form of the invention.
Figure 16:
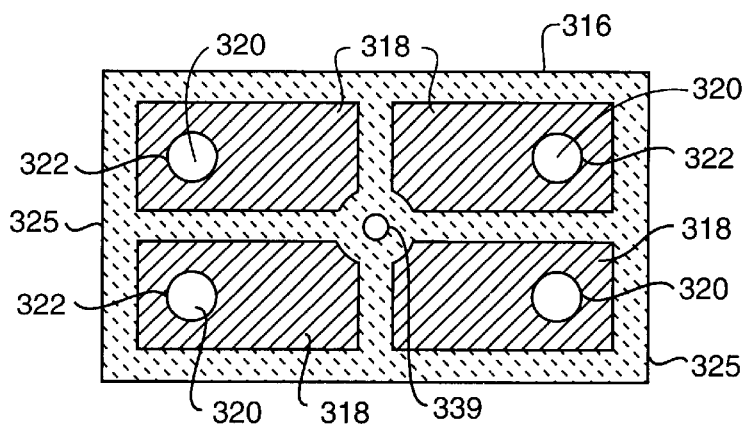
FIG. 16 is a sectional view taken generally on the line 16—16 of FIG. 15.
Figure 17:
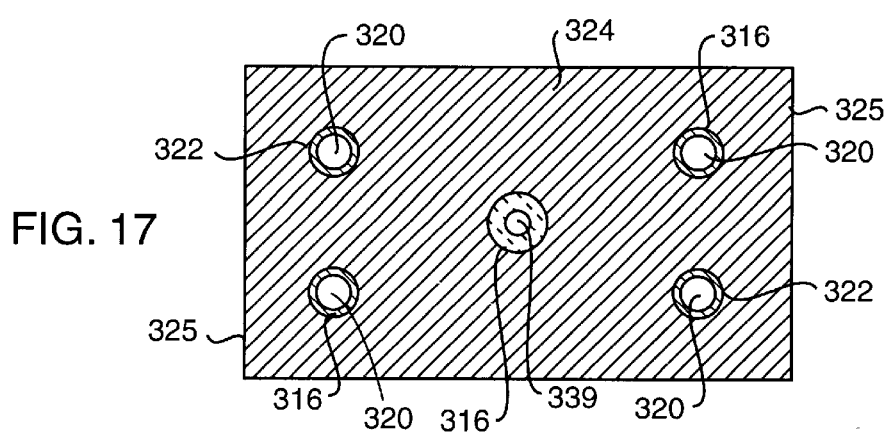
FIG. 17 is a sectional view taken generally on the line 17—17 of FIG. 15.

FIGS. 15–17 illustrate a rectangular quad polar configuration for a capacitor body adapted for use in a modified feedthrough capacitor filter assembly, wherein components corresponding structurally and functionally to those shown and described in FIGS. 1–4 are identified by common reference numerals increased by 300. In this embodiment, the modified capacitor body 316 has a generally rectangular shape with four feedthrough pin bores 320 extending therethrough generally within four separate quadrants thereof.

The pin bores 320 are each lined with a conductive surface metallization layer 322 (FIG. 16) or the like coupled with respective stacked groups of first or "active" electrode plates 318 formed in layers within the capacitor body 316. These stacked groups of "active" electrode plates 318 are arranged in an interleaved stacked array with a corresponding plurality of layers of second or "ground" electrode plates 324 which are spaced from the pin bores 320, but instead have outer edges exposed at one or more sides or ends of the rectangular capacitor body 316 for connection to a conductive surface metallization layer 325 (FIG. 17) or the like. A central leak detection passage 339 is formed in the capacitor body.

The capacitor body 316 shown in FIGS. 15–17 is adapted for assembly with a plurality of feedthrough terminal pins and an outer ferrule of appropriate rectangular shape, in the same manner as previously shown and described herein. In addition, the capacitor body 316 is associated with a hermetic seal (not shown in FIGS. 15–17) for sealing against passage of fluids through the ferrule and the associated connections with the capacitor body 316 and terminal pins. The leak detection passage 339 accommodates quick and efficient leak testing prior to use of the resultant feedthrough terminal pin assembly in an implantable medical device.

Figure 18:
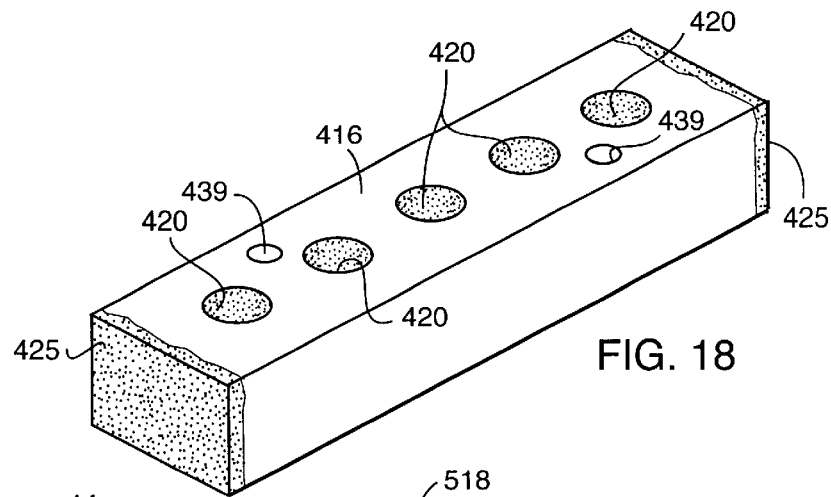
FIG. 18 is a perspective view of a capacitor showing features of still another modified preferred embodiment of the invention.

FIG. 18 illustrates an alternative geometry for a multi-lead capacitor body, identified by reference numeral 416, representing a variation of the capacitor body 316 illustrated in FIGS. 15–17. As shown, the modified capacitor body 416 has an elongated rectangular structure with five terminal pin bores 420 formed therein and arranged generally in an in-line or linear array. These pin bores 420 are lined with a conductive surface metallization layer or the like, for coupling individual terminal pins (not shown) with stacked layers of first or "active" electrode plates. While the "active" electrode plates are not depicted in FIG. 18, it will be recognized and understood that such plates are arranged in layers similar to the plates 318 of FIG. 16, but with the plates of each layer arranged in-line to correspond with the in-line array of pin bores 420. The "active" electrode plates are formed in an alternating stack with second or "ground" electrode plates (also not shown) having edges exposed and conductively connected to a surface metallization layer 425 or the like. FIG. 18 shows a pair of leak detection passages 439 formed through the capacitor body 416 at spaced locations along the capacitor body length. The capacitor body 416 is adapted for assembly with terminal pins and a suitably shaped ferrule (not shown), together with a hermetic seal (also not shown), and for quick and easy pressure testing of the hermetic seal by means of the pair of leak detection passages 439, all in the same manner as previously described.

Figure 19:
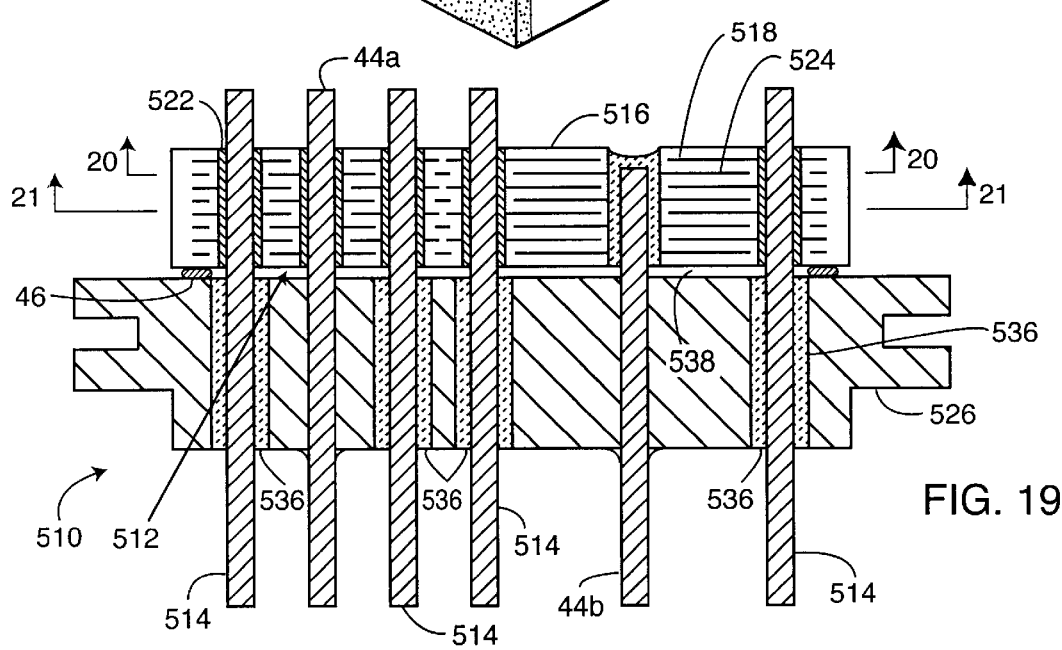
FIG. 19 is a sectional view similar to FIGS. 2, 6 and 9, but depicting a further alternative preferred embodiment of the invention.
Figure 20:
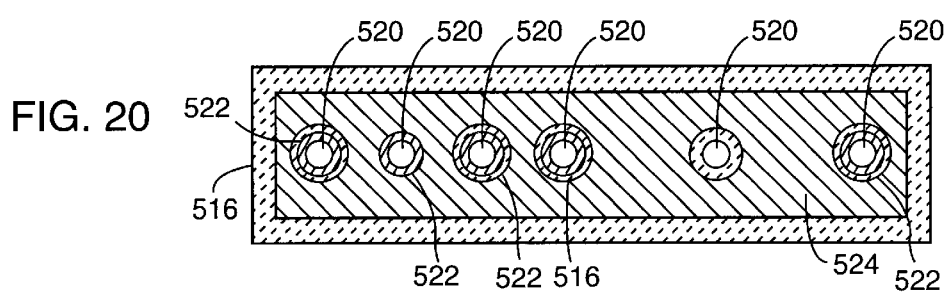
FIG. 20 is a sectional view taken generally on the line 20—20 of FIG. 19.
Figure 21:
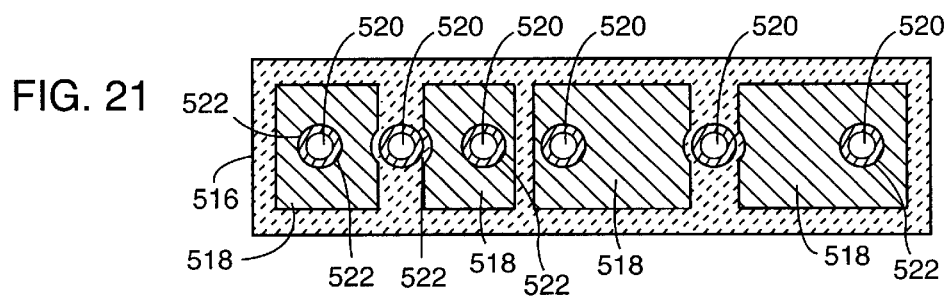
FIG. 21 is a sectional view taken generally on the line 21—21 of FIG. 19.

Another alternative preferred form of the invention is shown in FIGS. 19–21, wherein components corresponding structurally and functionally to those shown and described in FIGS. 1–4 are identified by common reference numerals increased by 500. FIGS. 19–20 illustrate a modified feedthrough capacitor filter assembly 510 in the form of an asymmetrical in-line quad polar EMI filter with internal ground.

More specifically, the modified filter assembly 510 includes a capacitor 516 which is spaced away from a hermetic ferrule 526 in such a way to provide for a clear passageway for helium leak detection. The four active quad polar terminal pins 514 are in nonconductive relation with the ferrule 526. This is accomplished by providing glass hermetic seals 536 individually around those portions of the terminal pins 514 extending through the ferrule 526.

In contrast with previously disclosed embodiments of the invention, there are two ground pins 44*a* and 44*b*, one of which extends all the way through the capacitor 516 and the other one which does not. Both of the ground pins 44*a* and 44*b* are in conductive relation with the ferrule 526. The two ground pins 44*a–b* are spaced in an ideal location to minimize internal ground electrode inductance. This means that the internal ground electrodes 524 will make an effective and efficient RF ground plane. If the capacitor 516 was built with only one grounded pin; for example, the right hand grounded pin 44*b*, then a substantial amount of inductance would be present across the ground plane.

With reference to FIG. 21 it will be noted that the active electrodes 518 for the two right-most terminal pins 514 are greater than the active area for the two left-most active terminal pins 514. This means that the capacitance will be higher for the two right-most pins 514 and accordingly, a higher level of EMI attenuation will be achieved. This is particularly desirable for example in the case of the sensing circuits of a cardiac pacemaker or implantable defibrillator, where the sensing circuits are inherently more susceptible to EMI signals, for example, as those caused by a hand-held cellular telephone. On the other hand, the lower capacitance and hence lower attenuation of the two left-most terminals 514 would not be a problem in the output circuitry of, for example, an implantable cardiac defibrillator or the output circuitry of a pacemaker because the output circuitry which produces a steady pulse or in the case of a high voltage implantable defibrillator, an occasional shock, is not nearly as sensitive to stray EMI signals. Accordingly, a lower level of attenuation is perfectly acceptable and sometimes desirable.

As was the case with previously described embodiments of the invention, the modified filter assembly 510 includes a rectangular-shaped capacitor body 516 formed to encase first or "active" electrode plates 518 in a stacked and alternating array with a corresponding number of second or "ground" electrode plates 524. The "active" electrode plates 518 include inner edges exposed along the lengths of axially extending bores 520 including a surface metallization layer 522 for conductively coupling the plates 518 in parallel to the conductive terminal pins 514. Similarly, the "ground" electrode plates 524 include inner edges exposed along the length of two axially extending bores 520 which also include a surface metallization layer 522 for conductively coupling the "ground" electrode plates 524 in parallel to the ground pins 44*a* and *b*. In this regard, a washer 46 (preferably dissolvable) is disposed between the hermetic seal 636 and the ferrule 626. The washer 46 insures that the axial gap 538, which effectively forms the vent 512, remains during assembly of the component parts of the assembly 610.

Figure 22:
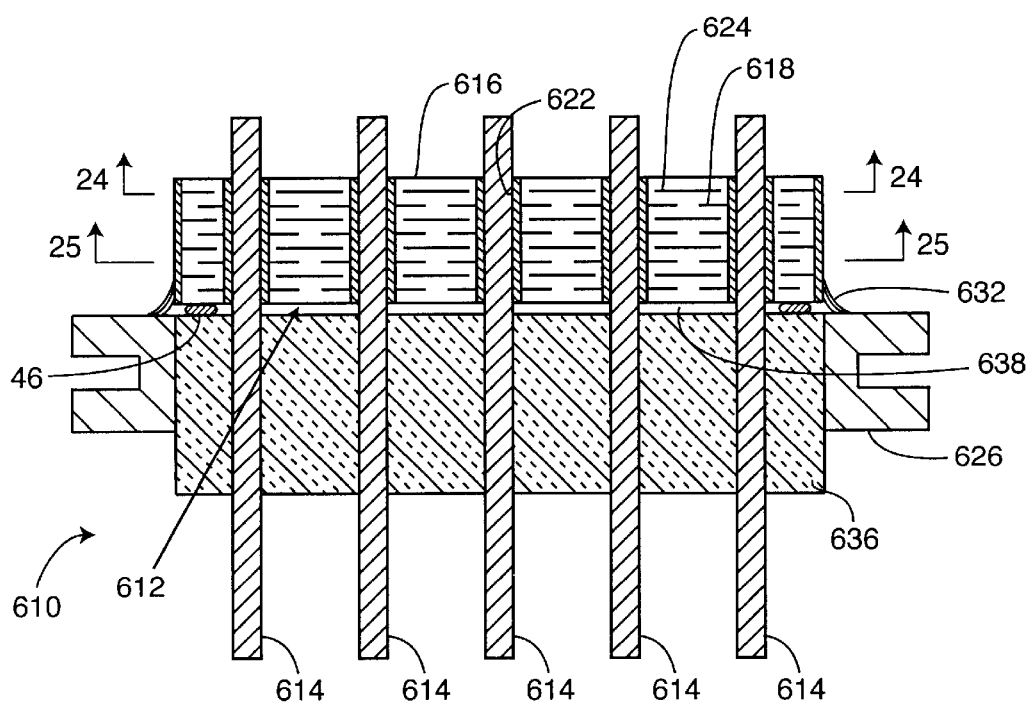
FIG. 22 is a sectional view similar to FIGS. 6, 9 and 19, but depicting a further alternative preferred embodiment of the invention.
Figure 23:
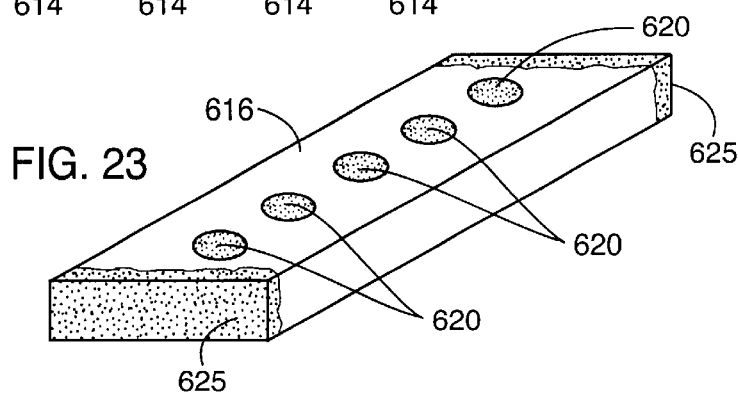
FIG. 23 is a perspective view of a capacitor utilized in the feedthrough capacitor filter assembly of FIG. 22.
Figure 24:
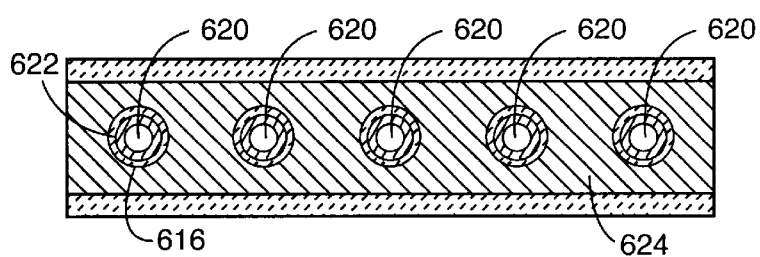
FIG. 24 is a sectional view taken generally along the line 24—24 of FIG. 22.
Figure 25:
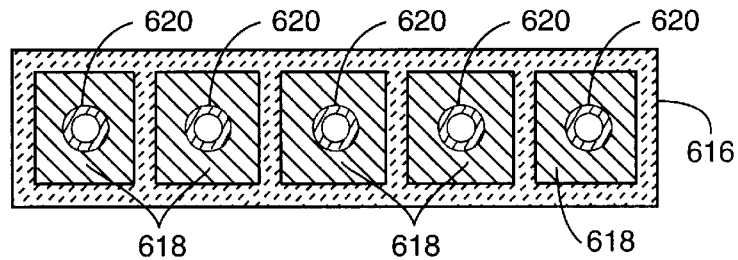
FIG. 25 is a sectional view taken generally along the line 25—25 of FIG. 22.
Figure 26:
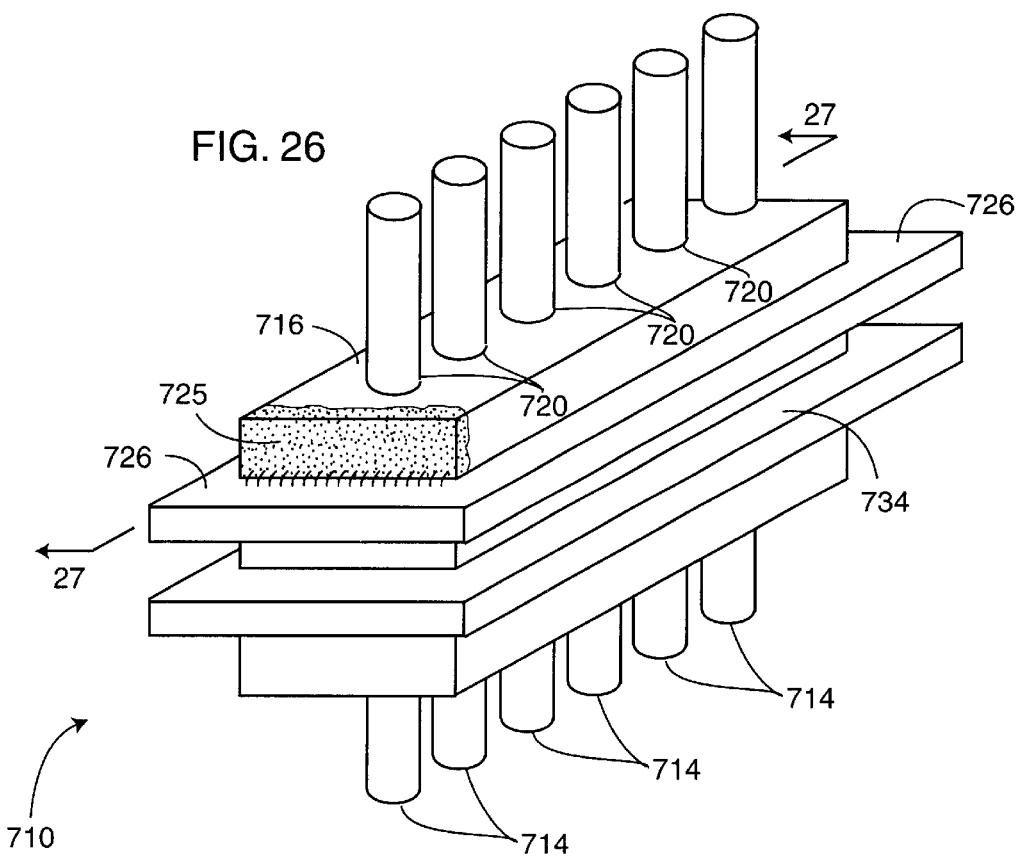
FIG. 26 is a perspective view similar to FIGS. 1 and 5, of a feedthrough filter capacitor assembly constructed in accordance with another alternative preferred embodiment of the invention.
Figure 27:
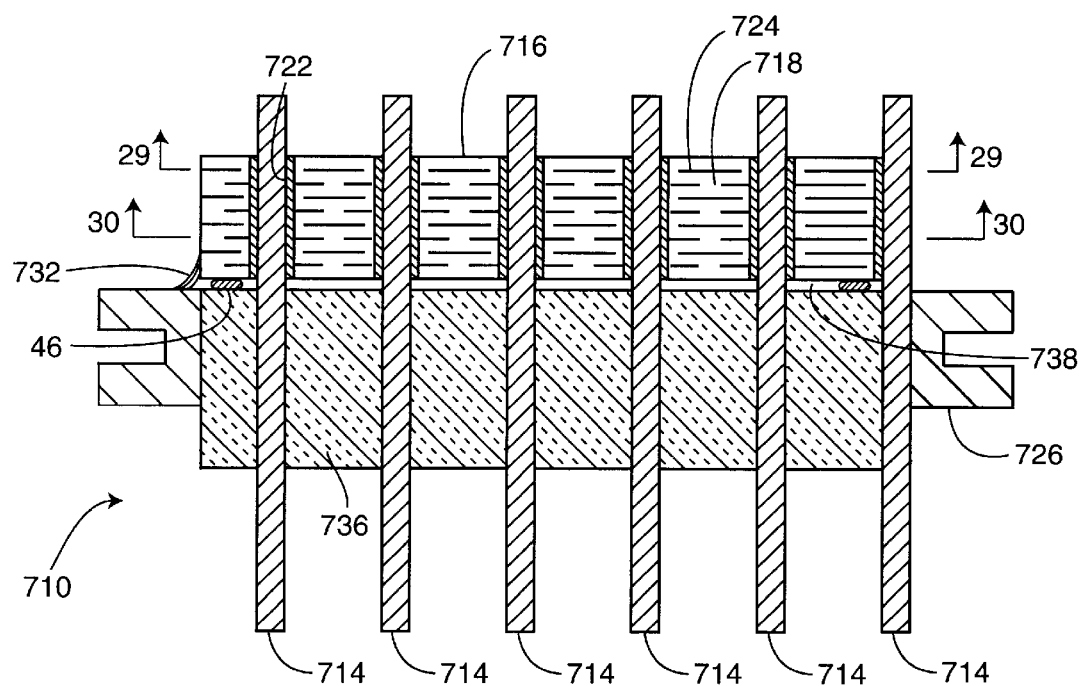
FIG. 27 is an enlarged sectional view taken generally on the line 27—27 of FIG. 26.
Figure 28:
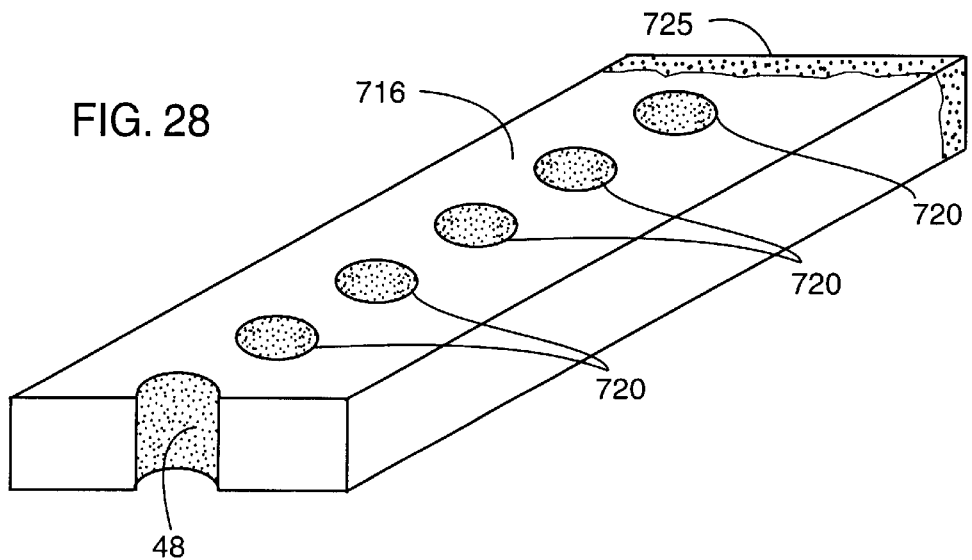
FIG. 28 is a perspective view of a capacitor utilized in connection with the feedthrough capacitor filter assembly of FIGS. 26 and 27.

FIGS. 22–24 illustrate yet another alternative preferred form of the invention, wherein components corresponding structurally and functionally to those shown and described in FIGS. 1–4 are identified by common reference numerals increased by 600. More specifically, the modified filter assembly 610 includes a rectangular-shaped capacitor body 616 formed to encase first or "active" electrode plates 618 in a stacked and alternating array with a corresponding number of second or "ground" electrode plates 624. The "active" electrode plates 618 include inner edges exposed along the length of five axially extending bores 620 which each include a surface metallization layer 622 for conductively coupling the plates 618 in parallel to the respective conductive terminal pins 614. The "ground" electrode plates 624 include outer edges exposed along the length of opposite sides of the capacitor body 616 which includes a surface metallization layer 625 for conductively coupling the plates 624 in parallel to an outer ferrule 626. In this regard, the outer ferrule 626 comprises a rectangular-shaped structure defining a central aperture 628 therethrough. The capacitor 614 is surface mounted to the ferrule 626. A conductive connection is made between the ferrule and the "ground" electrode plates 624 by means of a conductive braze 632 or the like between the ferrule and the surface metallization layer 625. A hermetic seal 636 is also positioned within the ferrule 626 at one axial side of the capacitor body 616, preferably to form a short axial gap 638 therebetween. In this regard, a washer 46 (preferably dissolvable) is disposed between the hermetic seal 636 and the ferrule 626. The washer 46 insures that the axial gap 138, which effectively forms the vent 612, remains during assembly of the component parts of the assembly 610.

FIGS. 26–30 illustrate yet another alternative preferred form of the invention, wherein components corresponding structurally and functionally to those shown and described in FIGS. 1–4 are identified by common reference numerals increased by 700. As was the case with the prior two embodiments, a washer 46 is provided between the capacitor 716 and the hermetic seal 736 to maintain the axial gap 738 therebetween. It is useful to have such axial gaps 738 for testing the filter assembly 610 quickly and reliably, in the same manner described above with the prior embodiments, to identify a defective hermetic seal 736 prior to installation of the filter assembly 610 into an implantable medical device or the like.

Figure 29:
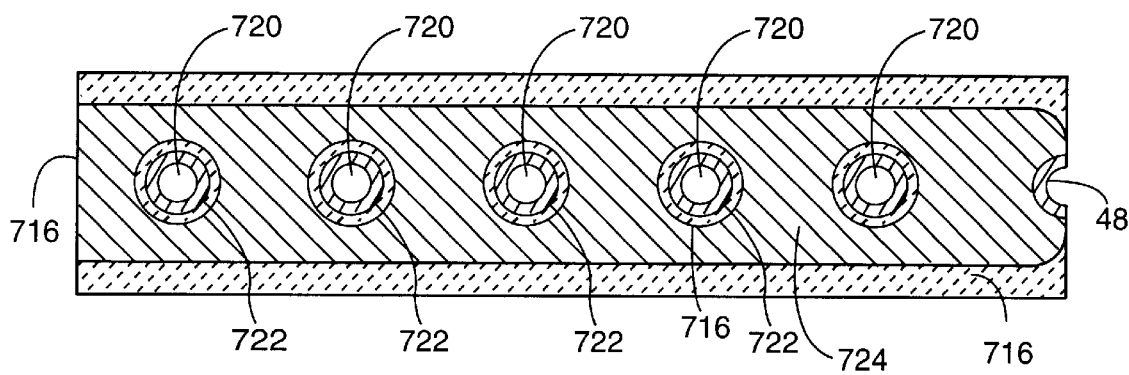
FIG. 29 is a sectional view taken generally along the line 29—29 of FIG. 27.
Figure 30:
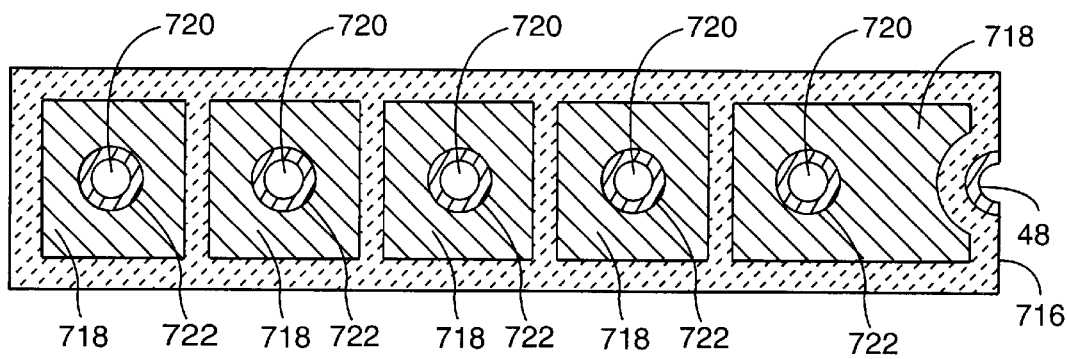
FIG. 30 is a sectional view taken generally along the line 30—30 of FIG. 27.

FIGS. 26–30 illustrate an in-line six-pole EMI filter capacitor 716 similar to those illustrated in FIGS. 19 and 22. However, the ground electrode plates 724 extend all the way through the capacitor 716 as illustrated in FIG. 29. Attachment to these ground electrode plates 724 is made on opposite ends rather than through lead wires as illustrated in FIGS. 19–21. On the right-most side of FIGS. 26, 27, 29 and 30, it can be seen that a semicircular notch 48 has been fashioned to receive at least a portion of a ground pin 44a which is in conductive relation with the ferrule 726. On the opposite end of the capacitor 716, which does not have said ground pin 44a, the entire end of the capacitor includes surface metallization 725 for coupling the stack of ground electrode plates 724 to one another and for conductively coupling said ground electrode plates to the ferrule 726.

The improved feedthrough capacitor filter assembly of the present invention thus provides, in a variety of potential configurations, an effective EMI filter assembly for an implantable medical device or the like wherein the integrity of the hermetic seal can be readily and reliably tested prior to patient implantation and use. The filter assembly incorporates a leak detection vent 12 which is formed to accommodate and facilitate post-assembly fluid leak testing of the hermetic seal, as by subjecting the hermetic seal to a selected pressurized test gas such as helium or the like, prior to implantation of the filter assembly in a medical device into a patient. In its most basic form, the leak detection vent comprises a gap 38–738 formed between facing surfaces of the capacitor and the hermetic seal. This gap may be supplemented with a leak detection passage formed directly into the monolithic capacitor body, wherein the leak detection passage is formed conveniently and in a manner consistent with automated production systems by convenient drilling, in a manner similar to the formation of the terminal pin bore or bores formed in the capacitor body. The filter assembly components are arranged for relatively simple orientation of the hermetic seal for exposure to the pressurized test gas, with any leaking gas accumulating within the gap between the hermetic seal and the capacitor body. From the gap, such leaking gas is free to flow to and through the leak detection passage where it can be detected quickly and easily by use of a suitable gas detection monitor.

A variety of further modifications and improvements in and to the improved feedthrough capacitor filter assembly of the present invention will be apparent to those persons skilled in the art. Accordingly, no limitation on the invention is intended by way of the foregoing description and accompanying drawings, except as set forth in the appended claims.

What is claimed is:

1. A feedthrough capacitor filter assembly, comprising:
 a capacitor body having first and second electrode plates encased therein in spaced relation, at least one terminal pin bore formed axially therethrough, and at least one leak detection passage extending axially therethrough;
 at least one conductive terminal pin extending through said at least one terminal pin bore in conductive relation with said first electrode plate;
 a conductive ferrule having at least one aperture formed axially therethrough, said capacitor body being mounted to said ferrule to extend across and close said at least one ferrule aperture with said second electrode plate in conductive relation with said ferrule; and
 at least one hermetic seal formed from a dielectric material and extending across and sealing said at least one ferrule aperture at one axial side of said capacitor body, said at least one hermetic seal defining an inboard face presented toward said capacitor body and an outboard face presented away from said capacitor body, said at least one terminal pin extending through said at least one hermetic seal;
 wherein said at least one leak detection passage vents said inboard face of said at least one hermetic seal.

2. The feedthrough capacitor filter assembly of claim 1, wherein said at least one hermetic seal and said capacitor body cooperatively define an axial gap formed therebetween.

3. The feedthrough capacitor filter assembly of claim 1, wherein said first and second electrode plates respectively comprise first and second sets of electrode plates encased in interleaved spaced relation within said capacitor body.

4. The feedthrough capacitor filter assembly of claim 1, wherein said capacitor body is formed from a substantially monolithic dielectric material.

5. The feedthrough capacitor filter assembly of claim 1, wherein said at least one terminal pin bore comprises a plurality of axially extending terminal pin bores formed in said capacitor body, and further wherein said at least one conductive terminal pin comprises a corresponding plurality of terminal pins extending respectively through said terminal pin bores and said at least one hermetic seal.

6. The feedthrough capacitor filter assembly of claim 5, wherein said at least one hermetic seal comprises a plurality of hermetic seals corresponding to a plurality of ferrule apertures.

7. The feedthrough capacitor filter assembly of claim 1, wherein one of said first and second electrode plates has an edge exposed within and lining said at least one leak detection passage.

8. The feedthrough capacitor filter assembly of claim 7, further including a conductive lining formed within said at least one leak detection passage.

9. The feedthrough capacitor filter assembly of claim 1, wherein said at least one leak detection passage is formed in said capacitor body in an axially centered position.

10. The feedthrough capacitor filter assembly of claim 1, wherein said at least one leak detection passage is formed in said capacitor body in an axially offset position.

11. The feedthrough capacitor filter assembly of claim 1, wherein said at least one leak detection passage is formed in said capacitor body as an offset enlargement of said at least one terminal pin bore.

12. The feedthrough capacitor filter assembly of claim 11, further including an insert member fitted within said at least one leak detection passage.

13. The feedthrough capacitor filter assembly of claim 12, wherein said insert member is removable.

14. The feedthrough capacitor filter assembly of claim 1, wherein said capacitor body has a generally discoidal shape.

15. The feedthrough capacitor filter assembly of claim 1, wherein said capacitor body has a generally rectangular shape.

16. The feedthrough capacitor filter assembly of claim 1, wherein said ferrule defines an internal shoulder for substantially nested reception of said capacitor body.

17. The feedthrough capacitor filter assembly of claim 1, including a dissolvable washer disposed between said at least one hermetic seal and said capacitor body to form an axial gap therebetween.

18. The feedthrough capacitor filter assembly of claim 1, further including conductive means for mounting said at least one terminal pin within said at least one terminal pin bore in conductive relation with said first electrode plate.

19. The feedthrough capacitor filter assembly of claim 1, including a plurality of axially extending terminal pin bores formed in said capacitor body, and at least one conductive ground pin extending into at least one of the plurality of axially extending terminal pin bores in conductive relation with said second electrode plate.

20. A feedthrough capacitor filter assembly, comprising:
   a capacitor body formed from a dielectric material encasing first and second sets of electrode plates in an interleaved spaced array, at least one terminal pin bore formed axially therethrough, and at least one leak detection passage extending axially therethrough;
   at least one conductive terminal pin extending through said at least one terminal pin bore in conductive relation with said first set of electrode plates;
   a conductive ferrule having at least one aperture formed axially therethrough, said capacitor body being mounted to said ferrule to extend across and close said at least one ferrule aperture with said second set of electrode plates in conductive relation with said ferrule; and
   at least one hermetic seal formed from a dielectric material and extending across and sealing said at least one ferrule aperture at one axial side of said capacitor body, said at least one hermetic seal defining an inboard face presented toward said capacitor body and an outboard face presented away from said capacitor body, said at least one terminal pin extending through said at least one hermetic seal;
   said at least one hermetic seal and said capacitor body cooperatively defining an axial gap formed therebetween;
   said at least one leak detection passage venting said gap.

21. The feedthrough capacitor filter assembly of claim 20, wherein said at least one terminal pin bore comprises a plurality of axially extending terminal pin bores formed in said capacitor body, and further wherein said at least one conductive terminal pin comprises a corresponding plurality of terminal pins extending respectively through said terminal pin bores and said at least one hermetic seal.

22. The feedthrough capacitor filter assembly of claim 21, wherein said at least one hermetic seal comprises a plurality of hermetic seals corresponding to a plurality of ferrule apertures.

23. The feedthrough capacitor filter assembly of claim 20, wherein one of said first and second electrode plates has an edge exposed within and lining said at least one leak detection passage.

24. The feedthrough capacitor filter assembly of claim 23, further including a conductive lining formed within said at least one leak detection passage.

25. The feedthrough capacitor filter assembly of claim 20, wherein said at least one leak detection passage is formed in said capacitor body as an offset enlargement of said at least one terminal pin bore.

26. The feedthrough capacitor filter assembly of claim 20, including a plurality of axially extending terminal pin bores formed in said capacitor body, and at least one conductive ground pin extending into at least one of the plurality of axially extending terminal pin bores in conductive relation with said second electrode plate.

27. The feedthrough capacitor filter assembly of claim 20, further including conductive means for mounting said capacitor body within said at least one ferrule aperture with said second set of electrode plates in conductive relation with said ferrule.

28. The feedthrough capacitor filter assembly of claim 20, further including conductive means for mounting said at least one terminal pin within said at least one terminal pin bore in conductive relation with said first set of electrode plates.

29. In a feedthrough capacitor filter assembly having a capacitor body with first and second electrode plates encased therein in spaced relation and at least one terminal pin bore formed axially therethrough, at least one conductive terminal pin extending through said at least one terminal pin bore in conductive relation with said first electrode plate, a conductive ferrule having at least one aperture formed axially therethrough, said capacitor body being mounted to said ferrule to extend across and close said at least one ferrule aperture with said second electrode plate in conductive relation with said ferrule, and at least one hermetic seal formed from a dielectric material and extending across and sealing said at least one ferrule aperture at one axial side of said capacitor body, said at least one hermetic seal defining an inboard face presented toward said capacitor body and an outboard face presented away from said capacitor body, said at least one terminal pin extending through said at least one hermetic seal, the improvement comprising:
   means for venting said inboard face of said at least one hermetic seal, wherein said capacitor body has at least one leak detection passage extending axially therethrough, said leak detection passage forming at least a portion of said venting means.

30. The improvement of claim 29, wherein said hermetic seal and said capacitor body cooperatively define an axial gap formed therebetween, said axial gap forming at least a portion of said venting means.

31. The improvement of claim 30, wherein said first and second electrode plates respectively comprise first and second sets of electrode plates encased in interleaved spaced relation within said capacitor body.

32. The improvement of claim 29, wherein one of said first and second electrode plates has an edge exposed within the lining said at least one leak detection passage.

33. The improvement of claim 32, further including a conductive lining formed within said at least one leak detection passage.

34. The improvement of claim 29, wherein said at least one leak detection passage is formed in said capacitor body as an offset enlargement of said at least one terminal pin bore.

35. The improvement of claim 34, further including an insert member fitted within said at least one leak detection passage.

36. The improvement of claim 35, wherein said insert member is removable.

37. A feedthrough filter capacitor, comprising:

a capacitor body having first and second electrode plates encased therein in spaced relation, and at least one terminal pin bore formed axially therethrough;

said capacitor body having at least one leak detection passage extending axially therethrough.

38. The feedthrough filter capacitor of claim 37, wherein said first and second electrode plates respectively comprise first and second sets of electrode plates encased in interleaved spaced relation within said capacitor body.

39. The feedthrough filter capacitor of claim 37, wherein said capacitor body is formed from a substantially monolithic dielectric material.

40. The feedthrough filter capacitor filter of claim 37, wherein said at least one terminal pin bore comprises a plurality of axially extending terminal pin bores formed in said capacitor body.

41. The feedthrough filter capacitor of claim 37, wherein one of said first and second electrode plates has an edge exposed within and lining said at least one leak detection passage.

42. The feedthrough filter capacitor of claim 41, further including a conductive lining formed within said at least one leak detection passage.

43. The feedthrough filter capacitor of claim 37, wherein said at least one leak detection passage is formed in said capacitor body in an axially centered position.

44. The feedthrough filter capacitor of claim 37, wherein said at least one leak detection passage is formed in said capacitor body in an axially offset position.

45. The feedthrough filter capacitor of claim 37, wherein said at least one leak detection passage is formed in said capacitor body as an offset enlargement of said at least one terminal pin bore.

46. The feedthrough filter capacitor of claim 45, further including an insert member fitted within said at least one leak detection passage.

47. The feedthrough filter capacitor of claim 46, wherein said insert member is removable.

48. The feedthrough filter capacitor of claim 37, wherein said capacitor body has a generally discoidal shape.

49. The feedthrough filter capacitor of claim 37, wherein said capacitor body has a generally rectangular shape.

50. A feedthrough capacitor filter assembly, comprising:

a capacitor body having first and second electrode plates encased therein in spaced relation, a plurality of terminal pin bores formed axially therethrough, and at least one leak detection passage extending axially therethrough;

at least one conductive terminal pin extending through at least one of the terminal pin bores in conductive relation with said first electrode plate;

a conductive ferrule having at least one aperture formed axially therethrough, said capacitor body being mounted to said ferrule to extend across and close said at least one ferrule aperture with said second electrode plate in conductive relation with said ferrule; and at least one hermetic seal formed from a dielectric material and extending across and sealing said at least one ferrule aperture at one axial side of said capacitor body, said at least one hermetic seal defining an inboard face presented towards said capacitor body and an outboard face presented away from said capacitor body, said at least one terminal pin extending through said hermetic seal, wherein said at least one hermetic seal and said capacitor body cooperatively define an axial gap formed therebetween.

51. The feedthrough capacitor filter assembly of claim 50, including a washer disposed between said at least one hermetic seal and said capacitor body.

52. The feedthrough capacitor filter assembly of claim 51, wherein said washer is dissolvable.

53. The feedthrough capacitor filter assembly of claim 50, including at least one conductive ground pin extending into at least one of the plurality of terminal pin bores in conductive relation with said second electrode plate.

54. The feedthrough capacitor filter assembly of claim 50, including a ground pin abutting and in conductive relation with both the ferrule and a conductive surface of the capacitor body.

55. The feedthrough capacitor filter assembly of claim 54, wherein the capacitor body includes a notch for receiving at least a portion of the ground pin therein, the notch including surface metallization for conductively coupling the ground pin to the second electrode plate.

56. The feedthrough capacitor filter assembly of claim 50, wherein the first and second electrode plates respectively comprise first and second sets of electrode plates encased in interleaved spaced relation within said capacitor body, and wherein said capacitor body is formed from a substantially monolithic dielectric material.

57. The feedthrough capacitor filter assembly of claim 50, wherein said at least one leak detection passage vents said gap.

* * * * *